United States Patent
Matsui et al.

(10) Patent No.: US 8,736,824 B2
(45) Date of Patent: May 27, 2014

(54) BLOOD ANALYSIS APPARATUS AND BLOOD ANALYSIS METHOD

(75) Inventors: Eriko Matsui, Tokyo (JP); Suguru Dowaki, Kanagawa (JP); Hirokazu Tatsuta, Tokyo (JP); Takeshi Kunihiro, Kanagawa (JP); Akira Niwa, Kyoto (JP); Megumu Saito, Kyoto (JP); Tatsutoshi Nakahata, Kyoto (JP)

(73) Assignees: Sony Corporation, Tokyo (JP); Kyoto University, Kyoto (JP)

( * ) Notice: Subject to any disclaimer, the term of this patent is extended or adjusted under 35 U.S.C. 154(b) by 0 days.

(21) Appl. No.: 13/561,820

(22) Filed: Jul. 30, 2012

(65) Prior Publication Data

US 2013/0038860 A1 Feb. 14, 2013

(30) Foreign Application Priority Data

Aug. 8, 2011 (JP) ................. P2011-172736

(51) Int. Cl.
  *G01N 33/38* (2006.01)
  *G01N 33/49* (2006.01)
  *G01N 15/05* (2006.01)
(52) U.S. Cl.
  CPC ............... *G01N 33/49* (2013.01); *G01N 15/05* (2013.01)
  USPC ............................................. 356/39; 356/40
(58) Field of Classification Search
  CPC ........................................................ G01N 33/49
  USPC ..................................................... 356/39–42
  See application file for complete search history.

(56) References Cited

U.S. PATENT DOCUMENTS

| 5,589,932 | A | 12/1996 | Garcia-Rubio et al. |
| 7,109,038 | B2 * | 9/2006 | Scholl et al. ............. 436/66 |
| 7,449,339 | B2 * | 11/2008 | Samsoondar et al. .......... 436/66 |
| 2003/0129754 | A1 | 7/2003 | Samsoondar |
| 2003/0232446 | A1 * | 12/2003 | Scholl et al. ............. 436/66 |
| 2005/0037505 | A1 * | 2/2005 | Samsoondar .......... 436/80 |
| 2005/0203356 | A1 | 9/2005 | Samsoondar |
| 2007/0222973 | A1 | 9/2007 | Hoshiko et al. |

FOREIGN PATENT DOCUMENTS

JP  2003-508765  3/2003

OTHER PUBLICATIONS

Extended European Search Report for EP application No. EP12005597 dated Apr. 26, 2013.
A direct relationship between adenosine triphosphate-level and in vivo viability of erythrocytes; Nature; 1962; vol. 194; Issue 4831; pp. 877-878.
Naotaka Hamasaki and Masaaki Yamamoto; Red Blood Cell Function and Blood Storage; Vox Sanguinis; 2000; 79; 191-197.
Helmut Marko et al.; UV-VIS and CD-Spectroscopic Investigations of Intermolecular Interactions of Bile Pigments with Small Proteins; Monatshefte fur Chemie; 120; 163-168; 1989.

* cited by examiner

*Primary Examiner* — Michael P Stafira
(74) *Attorney, Agent, or Firm* — Dentons US LLP (57) ABSTRACT

A blood analysis apparatus includes an analysis section. The analysis section is configured to compare a measurement spectrum obtained regarding red blood cells with a standard spectrum of heme, biliverdin, and bilirubin, and cause the measurement spectrum to belong to any one of the standard spectra.

7 Claims, 6 Drawing Sheets

BLOOD ANALYSIS APPARATUS AND BLOOD ANALYSIS METHOD

BACKGROUND

The present disclosure relates to a blood analysis apparatus and a blood analysis method, and more particularly, to a blood analysis apparatus, and the like, for evaluating a quality of blood using a degradation process of hemoglobin in red blood cells as an index.

Blood products including red blood cells for a blood transfusion are necessary for clinical treatment. It is an important issue to realize long-term storage of blood to use limited blood resources effectively. Two metabolic substances, that is, ATP (adenosine triphosphate) and 2, 3-bisphosphoglyceric acid (2, 3-BPG) are involved in life-span and an oxygen transport function of red blood cells. Concentrations of these substances in blood are known to decrease rapidly during blood storage and have been used as an index to evaluate a quality of stored blood.

In relation to the present disclosure, Japanese Unexamined Patent Application Publication No. 2003-508765 discloses a method and an apparatus for measuring characteristics of blood including hemoglobin (see also "A direct relationship between adenosine triphosphate-level and in vivo viability of erythrocytes.", Nature, 1962, Vol. 194, Issue 4831, pp.877-878, and "Red blood cell function and blood storage.", Vox Sanguinis, 2000, Vol.79, No.4, pp.191-197).

SUMMARY

There is a need for providing a new apparatus and method, which are capable of evaluating a quality of blood.

The inventors of the present disclosure obtained the ultraviolet-visible absorption spectrum of red blood cells and analyzed it. As a result, they found that a plurality of spectral patterns are detected for each red blood cell and similar spectral patterns are obtained in the measurements over time of the same red blood cells. Furthermore, they revealed that these spectral patterns correspond to the ultraviolet-visible absorption spectra of heme and its degradation products, biliverdin and bilirubin. The present disclosure is completed based on these findings.

Specifically, according to an embodiment of the present disclosure, there is provided a blood analysis apparatus including an analysis section configured to compare a measurement spectrum obtained regarding red blood cells with a standard spectrum of each of heme, biliverdin, and bilirubin, and cause the measurement spectrum to belong to any one of the standard spectra. Heme in red blood cells is degraded to biliverdin, and biliverdin is then degraded to bilirubin. Therefore, when a measurement spectrum obtained regarding red blood cells corresponds to any one of these spectra, it is possible to evaluate the degree of degradation of heme in the red blood cells and use the measurement spectrum as an index of time degradation of the red blood cells.

Favorably, in this blood analysis apparatus, the analysis section is configured to compare each measurement spectrum obtained in a plurality of areas of one red blood cell with the standard spectra, and calculate the number of measurement spectra caused to belong to the standard spectrum of heme, measurement spectra caused to belong to the standard spectrum of biliverdin, and measurement spectra caused to belong to the standard spectrum of bilirubin. More favorably, the analysis section is configured to calculate a ratio of at least one of the measurement spectra caused to belong to the standard spectrum of biliverdin and the measurement spectra caused to belong to the standard spectrum of bilirubin with respect to the measurement spectra caused to belong to the standard spectrum of heme.

The number or ratio can be an index of time degradation of red blood cells. Therefore, this blood analysis apparatus favorably includes a storage configured to store at least one of the measurement spectrum obtained regarding red blood cells for a predetermined period and one of the number and ratio of the measurement spectra caused to belong to the standard spectrum of one of heme, biliverdin, and bilirubin calculated for a predetermined period as time degradation information on the red blood cells.

Furthermore, in this blood analysis apparatus, the analysis section may identify the source of red blood cells based on one of the number and ratio of the measurement spectrum obtained regarding the red blood cells and/or the measurement spectra caused to belong to the standard spectrum of one of heme, biliverdin, and bilirubin.

In addition, according to an embodiment of the present disclosure, there is provided a blood analysis method including comparing a measurement spectrum obtained regarding red blood cells with a standard spectrum of each of heme, biliverdin, and bilirubin, and attributing the measurement spectrum to any one of the standard spectra.

This blood analysis method is capable of comparing each measurement spectrum obtained in a plurality of areas of one red blood cell with the standard spectra, calculating one of the number and ratio of measurement spectra caused to belong to the standard spectrum of heme, measurement spectra caused to belong to the standard spectrum of biliverdin, and measurement spectra caused to belong to the standard spectrum of bilirubin, and evaluating a quality of blood based on one of the calculated number and ratio.

This blood analysis method is capable of at least one of obtaining the measurement spectrum regarding red blood cells for a predetermined period and calculating one of the number and ratio of the measurement spectra caused to belong to the standard spectrum of one of heme, biliverdin, and bilirubin for a predetermined period, and evaluating time degradation of the red blood cells based on data thus obtained. Moreover, this blood analysis method is also capable of identifying the source of red blood cells based on one of the number and ratio of the measurement spectrum obtained regarding the red blood cells and/or the measurement spectra caused to belong to the standard spectrum of one of heme, biliverdin, and bilirubin.

In the present disclosure, "red blood cells" include red blood cells derived from a living body as well as artificial red blood cells derived from pluripotent stem cells such as iPS cells (induced Pluripotent Stem Cell: artificial pluripotent stem cells) and ES cells (Embryonic Stem Cell) and obtained by differentiation induction technology. It should be noted that, it is possible to perform establishment of iPS cells, for example, by an establishment method disclosed in Takahashi, K. and Yamanaka, S., Cell, 126: 663-676 (2006), and differentiation of red blood cells from pluripotent stem cells, for example, by a differentiation induction method disclosed in Shi-Jiang Lu, Qiang Feng, Jeniffer S. Park, Loyda Vida, Bao-Shiang Lee, Michael Strausbauch, Peter J. Wettstein, George R. Honig, Robert Lanza, blood, 112: 4475-4484 (2008).

According to the present disclosure, there is provided a new apparatus and method capable of evaluating a quality of blood.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, a favorable embodiment of the present disclosure will be described with reference to the drawings. It should be noted that the following embodiment is an example of a representative embodiment of the present disclosure, and does not limit the scope of the present disclosure.

Figure 1:
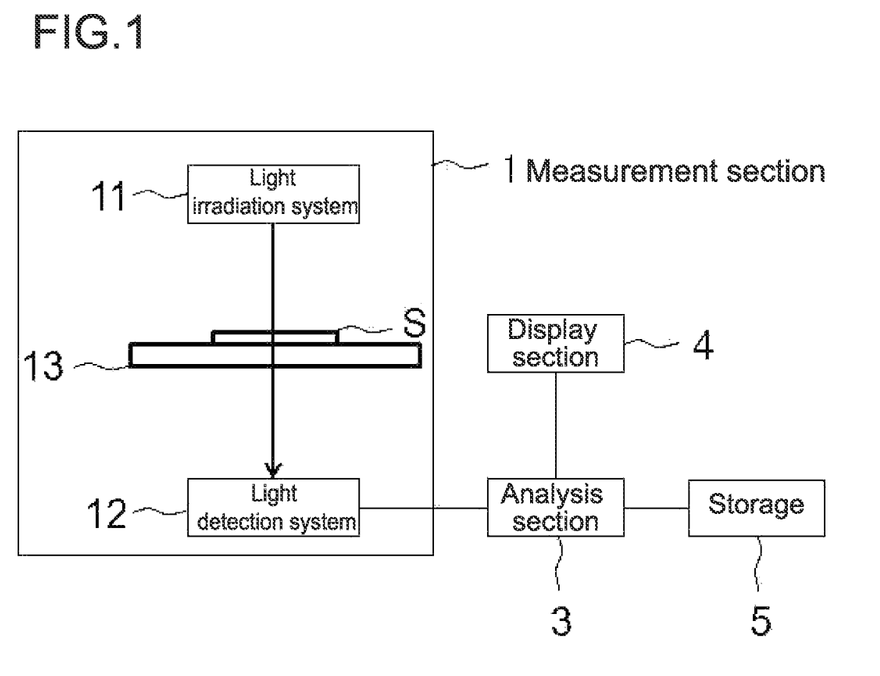
FIG. 1 is a schematic diagram for explaining a structure of a blood analysis apparatus according to an embodiment of the present disclosure.

A blood analysis apparatus according to an embodiment of the present disclosure can be constituted as a combination of a general-purpose phase-contrast microscope and a two-dimensional ultraviolet-visible spectrometer. The blood analysis apparatus includes a light irradiation system in which light in the ultraviolet region and the visible region is scanned with respect to blood sample S and is applied thereto, and a light detection system in which light transmitted through or reflected on the blood sample S is detected. FIG. 1 shows a structure of the blood analysis apparatus according to the embodiment of the present disclosure. A light irradiation system 11 is constituted of a light source, a mirror, a lens, and the like. On the other hand, a light detection system 12 is constituted of a lens, a diffractive element, a slit, a mirror, an image pickup device such as a CCD (Charge-Coupled Device) or a CMOS (Complementary Metal-Oxide Semiconductor), and the like. The light irradiation system 11 and the light detection system 12 constitute a measurement section 1. As shown in FIG. 1, the blood sample S is placed on a sample storing section 13. The sample storing section 13 holds the blood sample S in a state where light is applied from the light irradiation system 11 and light transmitted through or reflected on the blood sample S is conducted to the light detection system 12.

It is desirable to maintain a sealed environment in the sample storing section 13 so that dust and the like, which affect optical measurements, do not enter the inside of the sample storing section 13 from outside. The sample storing section 13 may be provided with a slot for drug administration to monitor a drug resistance and the like of the blood sample S or an instrument such as a clamp to select a specific sample in accordance with a degradation state of the blood sample S. The sample storing section 13 is not prevented from using a combination of techniques and art well known to those skilled in the art, in accordance with a measurement environment and an object.

According to the embodiment of the present disclosure, a case where the blood sample S is analyzed in a static in vitro environment will be described in detail. It should be noted that, as another embodiment, it is also possible to analyze the blood sample S while loading it from outside. In this case, for example, using a catheter, which does not block light in the visible region, an analysis environment disclosed in the embodiment of the present disclosure is applied after leading blood from a subject who needs an evaluation of a quality of blood in the body into the sample storing section 13. At this time, it becomes possible to perform a dynamic evaluation of a quality of blood without burden on the subject by maintaining a recirculation of blood from outside to inside the body.

This blood analysis apparatus includes an analysis section 3 which compares an ultraviolet-visible absorption spectrum (measurement spectrum) obtained regarding red blood cells with a standard spectrum of each of heme, biliverdin, and bilirubin stored in advance, and causes the measurement spectrum to belong to any one of the standard spectra. A standard spectrum may be stored in a storage 5 so that the analysis section 3 can read out the spectrum or may be stored in the analysis section 3.

As an algorithm to cause a measurement spectrum to belong to any one of standard spectra, a heretofore known algorithm is applicable. For example, an algorithm described below can be employed. When a value of (absorbance at wavelength of 650 nm)/(absorbance at wavelength of 380 nm) of a measurement spectrum is equal to or larger than $1/4$, the measurement spectrum is caused to belong to a standard spectrum of biliverdin. When a value of (absorbance at wavelength of 650 nm)/(absorbance at wavelength of 380 nm) of a measurement spectrum is smaller than $1/4$ and a value of (absorbance at wavelength of 550 nm)/(absorbance at wavelength of 420 nm) of the measurement spectrum is equal to or larger than $1/100$, the measurement spectrum is caused to belong to a standard spectrum of heme. When a value of (absorbance at wavelength of 550 nm)/(absorbance at wavelength of 420 nm) of a measurement spectrum is smaller than $1/100$, the measurement spectrum is caused to belong to a standard spectrum of bilirubin. It should be noted that an algorithm for attribution of a spectrum is not limited thereto.

The analysis section 3 is configured to compare each of a plurality of measurement spectra obtained in a plurality of areas of one red blood cell with a standard spectrum, and calculate the number or ratio of a measurement spectrum caused to belong to a standard spectrum of heme, a measurement spectrum caused to belong to a standard spectrum of biliverdin, and a measurement spectrum caused to belong to a standard spectrum of bilirubin. The calculated number or ratio is output to a display section 4 (e.g., display or printer) for display thereon.

The analysis section 3 determines a quality of blood based on the number or ratio of the obtained measurement spectrum and/or the measurement spectrum caused to belong to a standard spectrum of heme, biliverdin, or bilirubin. Heme is degraded to biliverdin and bilirubin successively. Therefore, it can be determined that degradation of heme in red blood cells is progressed and blood (or red blood cells) is deteriorated as the number or ratio of a measurement spectrum caused to belong to standard spectra/a standard spectrum of biliverdin and/or bilirubin increases with respect to a measurement spectrum caused to belong to a standard spectrum of heme. On the contrary, it can be determined that heme in red blood cells is preserved and blood is fresh, as the number or ratio described above decreases.

A determination result of a quality of blood by the analysis section 3 is also output to the display section 4 for display thereon. At this time, as Example to be described later, an operator can grasp a distribution of degradation or a rate of degradation in an area to be evaluated quickly or temporally by displaying information on a degradation state of blood as two-dimensional information (see FIG. 3). It thus becomes possible for an operator to select red blood cells in any degradation state from the blood sample S and take them from the sample storing section 13, using an instrument provided in the sample storing section 13 while confirming distribution of degradation of the blood sample S based on the two-dimensional information displayed on the display section 4 as an analysis image.

The storage 5 stores the number or ratio of a measurement spectrum obtained regarding red blood cells for a predetermined period and/or the measurement spectrum caused to belong to a standard spectrum of heme, biliverdin, or bilirubin calculated for a predetermined period as time degradation information on red blood cells. The time degradation information may be the one obtained or calculated successively or intermittently for a predetermined period.

An operator can follow a time degradation process as a behavior of red blood cells in more detail in a manner of fixed-point observation, based on the number of ratio of a measurement spectrum stored as time degradation information and/or a measurement spectrum caused to belong to a standard spectrum of heme, biliverdin, or bilirubin. Accordingly, it becomes possible to apply the information to a diagnosis of hemoglobinopathy and the like due to abnormal oxidation of iron such as methemoglobinemia, or function analysis of red blood cells derived from a genetic hemoglobinopathy, and the like.

In this case, the analysis section 3 or the storage 5 stores a spectral pattern appearing in a specific disease peculiarly or the number or ratio of a spectrum caused to belong to a standard spectrum of heme, biliverdin, or bilirubin so that the diagnosis can be made regardless of how an operator is skilled. Then, the analysis section 3 identifies a state of a disease by reading out these data and comparing them with measurement data. The result is then output on the display section 4.

Moreover, the analysis section 3 may identify cell source from which red blood cells are derived, based on the number or ratio of a measurement spectrum obtained regarding red blood cells and/or a measurement spectrum caused to belong to a standard spectrum of heme, biliverdin, or bilirubin. Also in this case, the analysis section 3 or the storage 5 stores a spectral pattern appearing in red blood cells derived from a specific cell or the number or ratio of a spectrum caused to belong to a standard spectrum of heme, biliverdin, or bilirubin. Then, the analysis section 3 identifies cell source from which red blood cells are derived, by reading out these data and comparing them with measurement data. The result is then output on the display section 4.

It should be noted that the blood analysis apparatus according to the embodiment of the present disclosure can also evaluate physical properties of red blood cells differentiated of iPS cells by comparing red blood cells derived from a living body with red blood cells derived from iPS cells while capturing a cell deformation of the red blood cells when exposed in various stressful environments in which osmotic pressure, pH, concentrations of oxygen, and the like are adjusted, and denaturation of hemoglobin associated with the cell deformation.

The blood analysis apparatus according to the embodiment of the present disclosure may also be structured as follows.

(1) A blood analysis apparatus, including
an analysis section configured to compare a measurement spectrum obtained regarding red blood cells with a standard spectrum of each of heme, biliverdin, and bilirubin, and cause the measurement spectrum to belong to any one of the standard spectra.

(2) The blood analysis apparatus according to (1) above, in which
the analysis section compares each measurement spectrum obtained in a plurality of areas of one red blood cell with the standard spectra, and calculates the number of measurement spectra caused to belong to the standard spectrum of heme, measurement spectra caused to belong to the standard spectrum of biliverdin, and measurement spectra caused to belong to the standard spectrum of bilirubin.

(3) The blood analysis apparatus according to (1) or (2) above, in which
the analysis section calculates a ratio of at least one of the measurement spectra caused to belong to the standard spectrum of biliverdin and the measurement spectra caused to belong to the standard spectrum of bilirubin with respect to the measurement spectra caused to belong to the standard spectrum of heme.

(4) The blood analysis apparatus according to (1) to (3) above, further including
a storage configured to store at least one of the measurement spectrum obtained regarding red blood cells for a predetermined period and one of the number and ratio of the measurement spectra caused to belong to the standard spectrum of one of heme, biliverdin, and bilirubin calculated for a predetermined period as time degradation information on the red blood cells.

(5) The blood analysis apparatus according to (1) to (4) above, in which
the analysis section identifies source of red blood cells based on one of the number and ratio of the measurement spectrum obtained regarding the red blood cells and/or the measurement spectra caused to belong to the standard spectrum of one of heme, biliverdin, and bilirubin.

Further, a blood analysis method according to an embodiment of the present disclosure may be structured as follows.

(1) A blood analysis method, including
comparing a measurement spectrum obtained regarding red blood cells with a standard spectrum of each of heme, biliverdin, and bilirubin, and attributing the measurement spectrum to any one of the standard spectra.

(2) The blood analysis method according to (1) above, further including:
comparing each measurement spectrum obtained in a plurality of areas of one red blood cell with the standard spectra;
calculating one of the number and ratio of measurement spectra caused to belong to the standard spectrum of heme, measurement spectra caused to belong to the standard spectrum of biliverdin, and measurement spectra caused to belong to the standard spectrum of bilirubin; and
evaluating a quality of blood based on one of the calculated number and ratio.

(3) The blood analysis method according to (1) or (2) above, further including
at least one of obtaining the measurement spectrum regarding red blood cells for a predetermined period and calculating one of the number and ratio of the measurement spectra caused to belong to the standard spectrum of one of heme, biliverdin, and bilirubin for a predetermined period, and evaluating time degradation of the red blood cells based on data thus obtained.

(4) The blood analysis method according to (1) to (3) above, further including
identifying source of red blood cells based on one of the number and ratio of the measurement spectrum obtained regarding the red blood cells and/or the measurement spectra caused to belong to the standard spectrum of one of heme, biliverdin, and bilirubin.

EXAMPLE

An observation of red blood cells was conducted using a phase-contrast microscope (TE2000, Nikon Corp.) and a two-dimensional visible spectrometer (in-house product). Obtained ultraviolet-visible absorption spectra are shown in FIG. 2. Moreover, it was confirmed that an absorption peak is not detected from only a buffer solution with suspended red blood cells.

Figure 2A:
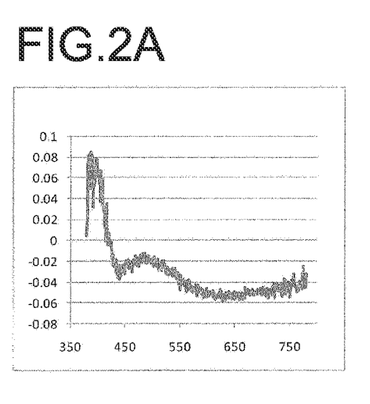
FIGS. 2 are graphs as drawing substitutes each showing an ultraviolet-visible absorption spectrum obtained from red blood cells according to Example of the present disclosure.
Figure 2B:
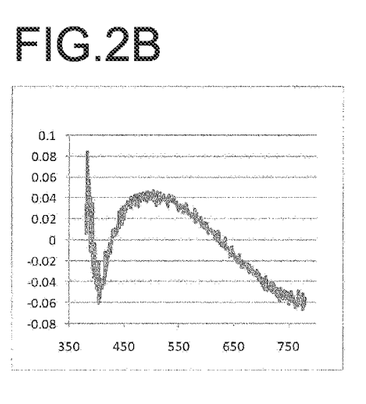
Figure 2C:
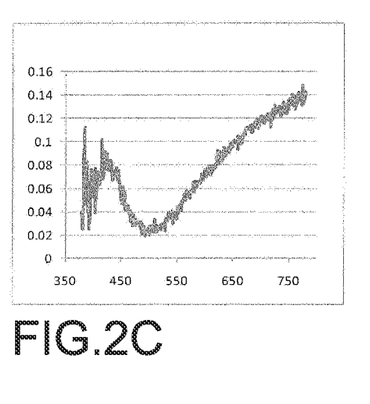
Figure 3A:
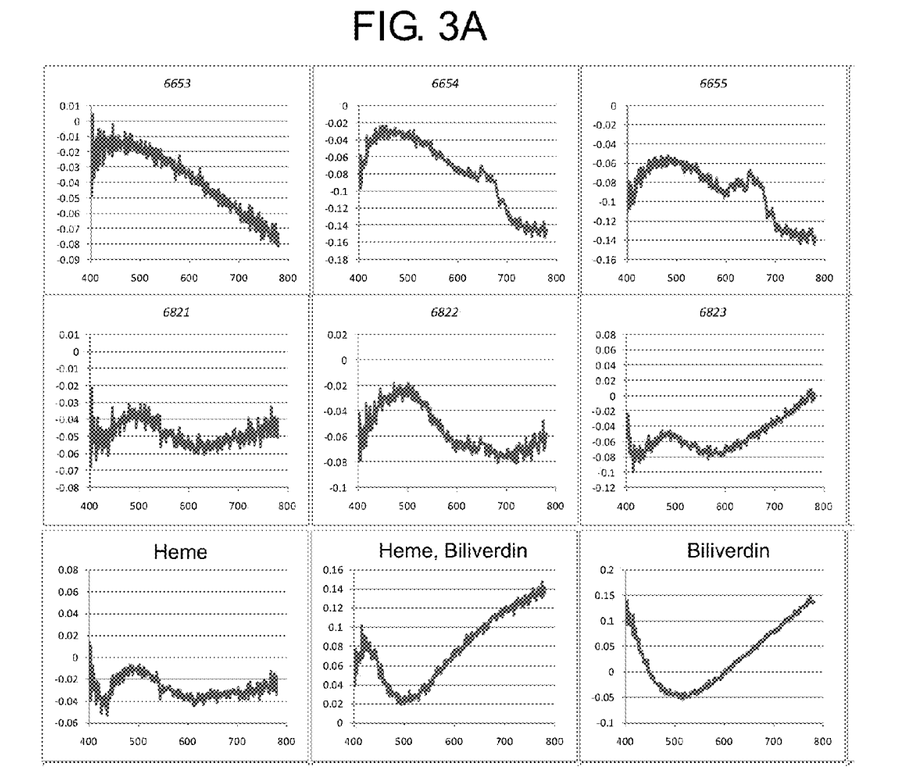
FIG. 3 is a graph as a drawing substitute showing a matrix of ultraviolet-visible absorption spectra obtained in a plurality of areas of one red blood cell according to Example of the present disclosure.
Figure 3B:
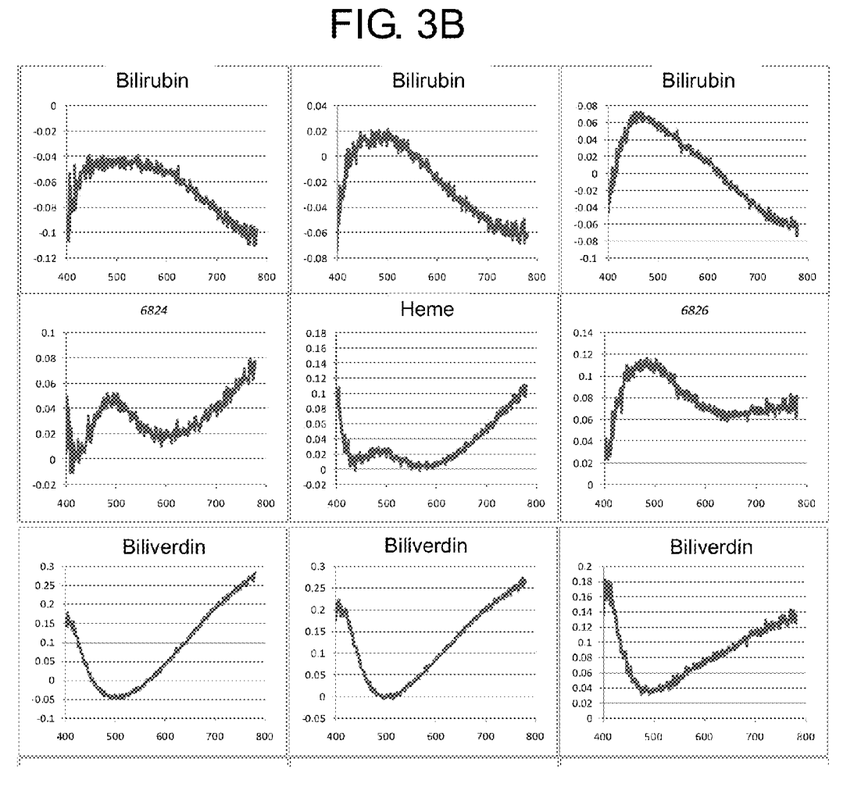
Figure 3C:
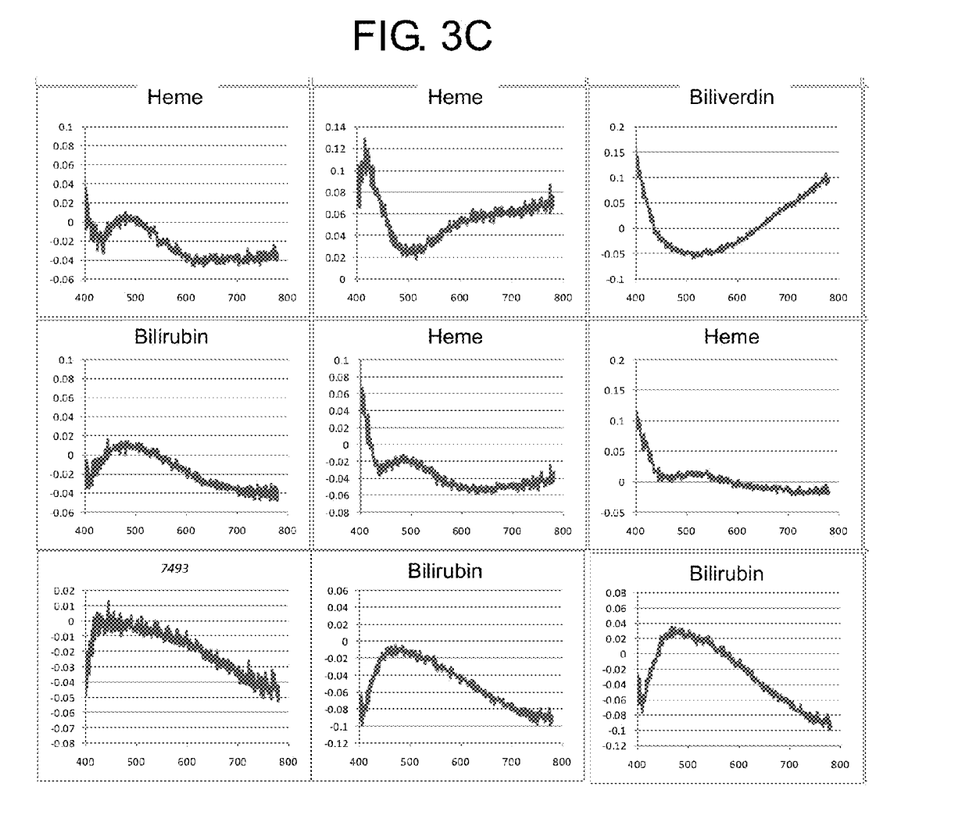
Figure 3D:
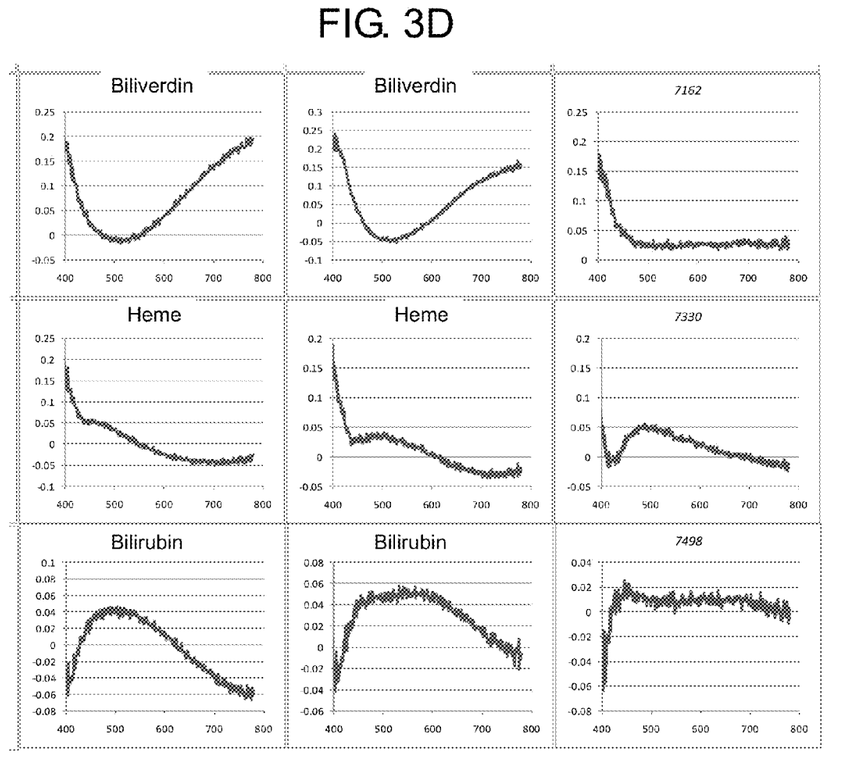

FIGS. 2A to 2C each show an ultraviolet-visible absorption spectrum obtained from different red blood cells. These spectra appeared also in a case where ultraviolet rays were continued to be applied onto red blood cells and an ultraviolet-visible absorption spectrum of the same red blood cell was measured temporally. Specifically, the spectrum shown in FIG. 2A was observed at first and it became the one shown in FIG. 2B or 2C subsequently.

Hemoglobin is composed of heme iron complex and globin. Heme iron complex is known to be derived from a porphyrin ring which surrounds an atom of iron and show an absorption spectrum characterized by a Soret absorption band at the wavelength of about 400 nm and a Q absorption band at the wavelength of about 550 nm. Since an ultraviolet-visible absorption spectrum shown in FIG. 2A matched a spectrum of reduced hemoglobin, it was considered to correspond to an ultraviolet-visible absorption spectrum of heme. On the other hand, ultraviolet-visible absorption spectra shown in FIGS. 2B and 2C matched spectra of bilirubin and biliverdin described in "UV-VIS and CD-spectroscopic investigations of intermolecular interactions of bile pigments with small proteins.", Monatshefte fur Chemie/Chemical Monthly, 1989, Vol.120, No.2, pp.163-168, respectively.

An ultraviolet-visible absorption spectrum of red blood cells being degraded by irradiation with ultraviolet rays was changed from the spectrum of heme (FIG. 2A) obtained at first to the spectrum of bilirubin or biliverdin (FIGS. 2B and 2C, respectively). This indicates that a degree of degradation of heme in red blood cells can be evaluated based on the ultraviolet-visible absorption spectrum of the red blood cells and used as an index of time degradation of the red blood cells.

FIG. 3 is a graph as a drawing substitute showing a matrix of ultraviolet-visible absorption spectra obtained in a plurality of areas of one red blood cell. A spectrum corresponding to heme, biliverdin, or bilirubin is detected in each area. Therefore, it can be seen that the degree of degradation of heme in one red blood cell can be determined with high accuracy, based on the number or ratio of a spectrum corresponding to heme and a measurement spectrum corresponding to biliverdin or bilirubin. Further, as described above, it is found that a distribution of degradation or a rate of degradation in an area to be evaluated can be grasped quickly or temporally by obtaining information on a degradation state of blood as two-dimensional information using the degree of degradation of heme.

It should be noted that, although FIG. 3 shows an example of a matrix of ultraviolet-visible absorption spectra obtained by magnifying one red blood cell, it is also possible to get a matrix of ultraviolet-visible absorption spectra obtained from a plurality of red blood cells at a low magnification. In this case, it becomes possible to obtain two-dimensional information by which a distribution of degradation or a rate of degradation of a plurality of red blood cells included in blood sample can be grasped quickly or temporarily, and information on a degradation state of the entire blood sample by the degree of degradation of heme.

According to the embodiment of the present disclosure, it is possible to evaluate the degree of degradation of heme in red blood cells by an ultraviolet-visible absorption spectrum obtained regarding the red blood cells and obtain an index of time degradation of the red blood cells. Therefore, the present disclosure is used for, for example, an evaluation of a quality of stored blood or a drug therapy monitoring, and is applicable to an extracorporeal circulation dialysis apparatus, a blood gas measurement apparatus, a blood clotting evaluation apparatus, an apparatus for testing for occult blood, and the like.

The present disclosure contains subject matter related to that disclosed in Japanese Priority Patent Application JP 2011-172736 filed in the Japan Patent Office on Aug. 8, 2011, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A blood analysis apparatus, comprising:
an analysis section configured to (i) compare a measurement spectrum obtained regarding red blood cells with a standard spectrum of each of heme, biliverdin, and bilirubin, (ii) cause the measurement spectrum to belong to any one of the standard spectra, (iii) compare each measurement spectrum obtained in a plurality of areas of one red blood cell with the standard spectra, (iv) calculate one of a number and ratio of (a) measurement spectra caused to belong to the standard spectrum of heme, (b) measurement spectra caused to belong to the standard spectrum of biliverdin, and (c) measurement spectra caused to belong to the standard spectrum of bilirubin; and (v) output a quality of blood based on the calculated number or ratio.

2. The blood analysis apparatus according to claim 1, wherein, the analysis section is configured to calculate one of the number and ratio based on at least one of the measurement spectra caused to belong to the standard spectrum of biliverdin and the measurement spectra caused to belong to the standard spectrum of bilirubin with respect to the measurement spectra caused to belong to the standard spectrum of heme.

3. The blood analysis apparatus according to claim 2, further comprising a storage configured to store at least one of the measurement spectrum obtained regarding red blood cells for a predetermined period and one of the number and ratio of the measurement spectra caused to belong to the standard spectrum of one of heme, biliverdin, and bilirubin calculated for a predetermined period as time degradation information on the red blood cells.

4. The blood analysis apparatus according to claim 2, wherein the analysis section is configured to identify a source of the red blood cells based on one of the number and ratio of the measurement spectrum obtained regarding the red blood cells and/or the measurement spectra caused to belong to the standard spectrum of one of heme, biliverdin, and bilirubin.

5. A blood analysis method, comprising the steps of: comparing a measurement spectrum obtained regarding red blood cells with a standard spectrum of each of heme, biliverdin, and bilirubin; attributing the measurement spectrum to any one of the standard spectra; comparing each measurement spectrum obtained in a plurality of areas of one red blood cell with the standard spectra; calculating one of a number and ratio of measurement spectra caused to belong to the standard spectrum of heme, measurement spectra caused to belong to the standard spectrum of biliverdin, and measurement spectra caused to belong to the standard spectrum of bilirubin; and outputting a quality of blood based on one of the calculated number and ratio.

6. The blood analysis method according to claim 5, further comprising at least one of obtaining the measurement spectrum regarding red blood cells for a predetermined period and calculating one of the number and ratio of the measurement spectra caused to belong to the standard spectrum of one of heme, biliverdin, and bilirubin for a predetermined period, and evaluating time degradation of the red blood cells based on data thus obtained.

7. The blood analysis method according to claim 5, further comprising identifying a source of the red blood cells based on one of the number and ratio of the measurement spectrum obtained regarding the red blood cells and/or the measurement spectra caused to belong to the standard spectrum of one of heme, biliverdin, and bilirubin.

* * * * *